United States Patent [19]

Grélat et al.

[11] 4,198,529

[45] Apr. 15, 1980

[54] PROCESS FOR THE PRODUCTION OF ALKOXY-SUBSTITUTED POLYCYCLIC AROMATIC COMPOUNDS

[75] Inventors: Maurice Grélat, Bettingen; Claus D. Weis, Pfeffingen, both of Switzerland

[73] Assignee: Ciba-Geigy Corporation, Ardsley, N.Y.

[21] Appl. No.: 1,573

[22] Filed: Jan. 8, 1979

[30] Foreign Application Priority Data

Jan. 11, 1978 [CH] Switzerland ............... 278785/78

[51] Int. Cl.$^2$ ................. C07C 5/327; C07C 5/09
[52] U.S. Cl. .................. 568/633; 260/355; 260/352; 260/359; 260/360; 260/364; 260/383; 260/396 R
[58] Field of Search ............... 260/355, 358, 352, 359, 260/360, 364, 383, 396 R; 568/633

[56] References Cited

U.S. PATENT DOCUMENTS

2,935,518  5/1960  Reetz ........................ 260/396 R

FOREIGN PATENT DOCUMENTS

2533428  2/1977  Fed. Rep. of Germany.
311661  5/1930  United Kingdom.

OTHER PUBLICATIONS

*Bule. Chem. Soc.* Japan, vol. 49, pp. 283 & 284, 1976.

*Primary Examiner*—Winston A. Douglas
*Assistant Examiner*—Raymond K. Covington
*Attorney, Agent, or Firm*—Prabodh I. Almaula

[57] ABSTRACT

The invention provides a process for the production of alkoxy-substituted polycyclic aromatic compounds from corresponding hydroxy-substituted compounds.

5 Claims, No Drawings

PROCESS FOR THE PRODUCTION OF ALKOXY-SUBSTITUTED POLYCYCLIC AROMATIC COMPOUNDS

The present invention provides a process for the production of alkoxy-substituted polycyclic aromatic compounds.

The production of alkoxy-substituted polycyclic compounds by alkylation of the corresponding hydroxy compounds with conventional alkylating agents is known from the literature (cf. Fiat Final Report No. 1313, Vol. II, pp. 86–87).

The alkylation, especially the methylation, with sulfonic acid esters is expensive and must be carried out in an anhydrous medium. The alkylation with dialkyl sulfates, especially dimethyl sulfate, has a number of drawbacks because of the properties of the compounds.

It has now been found that hydroxy-substituted polycyclic aromatic compounds can be alkylated in good yield with dialkyl alkanephosphonates while avoiding the drawbacks referred to above.

The process of the present invention for the production of alkoxy-substituted polycyclic aromatic compounds of the formula

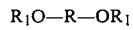

wherein R is an unsubstituted or substituted polycyclic aromatic radical and $R_1$ is an alkyl radical of 1 to 4, preferably 1 or 2, carbon atoms, comprises reacting a polycyclic aromatic compound of the formula

wherein R is defined above, with a dialkyl alkanephosphonate of the formula

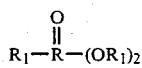

wherein $R_1$ is as defined above.

Examples of eligible polycyclic aromatic radicals R are the naphthylene, anthrylene, 2,7-phenanthrylene, 16,17-violanthrylene radical, an isoviolanthrylene radical, a pyranthrylene radical, an anthanthrylene radical or a m- or p-oligophenylene radical.

Eligible substituents of the radicals R are chiefly halogen atoms, preferably chlorine or bromine atoms.

The reaction can be carried out in the presence or absence of a base. Preferably, the reaction is carried out in the presence of a base or of a mixture of bases.

Preferred bases are alkali metal carbonates and bicarbonates, for example those of sodium and potassium, tertiary amines, for example trialkylamines, preferably triethylamines or trialkanolamines, preferably triethanolamine, N,N-dimethyl aniline, or mixtures of such bases.

The reaction can furthermore be carried out in the presence or absence of solvents or diluents. If an excess of the dialkyl alkane-phosphonate is used, then this latter acts simultaneously as solvent and the presence of other solvents or diluents is thus not necessary.

Suitable solvents or diluents are conventional solvents which are inert to the reactants, for example nitrobenzene or trichlorobenzene, or compounds which are liquid at the reaction temperature, such as naphthalene.

The reaction temperatures are from 130° to 230° C., preferably from 150° to 210° C.

Of particular interest is the production of the compound of the formula

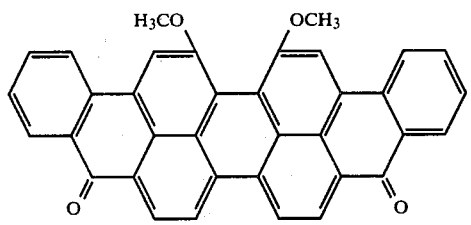

by reaction of the compound of the formula

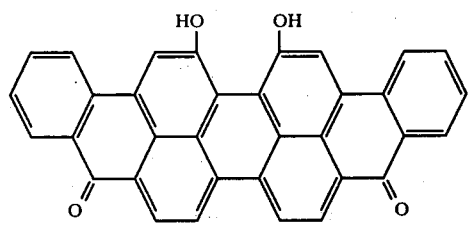

with dimethyl methanephosphonate of the formula

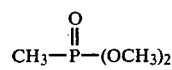

The compounds which can be obtained by the process of the invention are valuable intermediates for the manufacture of dyes or constitute dyes or scintillators [cf. British patent specification 311,661 and Chemiker Zeitung 15, 517 ff. (1965)].

The invention is illustrated by the following Examples, in which the percentages are by weight.

EXAMPLE 1

2.5 g of N,N-dimethyl aniline and 30 g of 16,17-dihydroxyviolanthrone of the formula

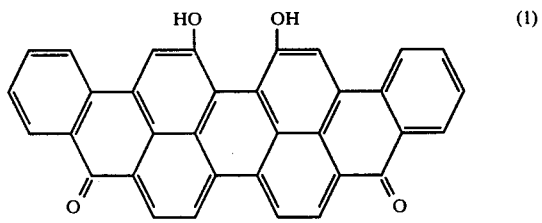

45 g of sodium carbonate and 60 g of dimethylmethane phosphonate are added to 120 g of nitrobenzene. With stirring, the reaction mixture is heated in the course of 2 hours to 200° C. and reacted for 4 hours at this temperature, during which time a small amount of water is distilled off. The reaction mixture is cooled to 80°–100° C. and the precipitate is filtered with suction. The residue is distilled with steam, affording in good yield the green vat dye of the formula

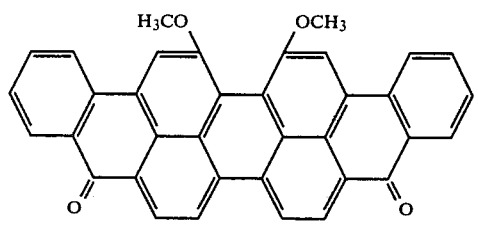

in the form of bronze-coloured crystals.

EXAMPLE 2

With stirring, 19 parts of 16,17-dihydroxyviolanthrone, 50 parts of sodium carbonate, 2 parts of N,N-dimethyl aniline and 120 parts of dimethyl methanephosphonate are heated to 50° C. and stirred for 1 hour at this temperature. The temperature of the reaction mixture is raised to 130° C. and then after 30 minutes to 170°–175° C. The reaction mixture is kept at this temperature for 6 hours. The water which has formed is removed by distillation. The dye is collected by filtration at 90°–100° C. and washed with warm dimethyl methanephosphonate. The crude filter cake is boiled with water, filtered with suction, washed neutral and dried, affording in good yield the bronze-coloured crystalline product of formula (2), which dyes cotton green from a blue vat.

What is claimed:

1. A process for the production of alkoxy-substituted polycyclic aromatic compounds of the formula

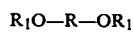

wherein R is an unsubstituted or substituted polycyclic aromatic radical and $R_1$ is an alkyl radical of 1 to 4 carbon atoms, which comprises reacting a polycyclic aromatic compound of the formula

wherein R is as defined above, with a dialkyl alkanephosphonate of the formula

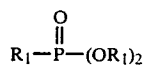

wherein $R_1$ is as defined above.

2. A process according to claim 1 for the production of the compound of the formula

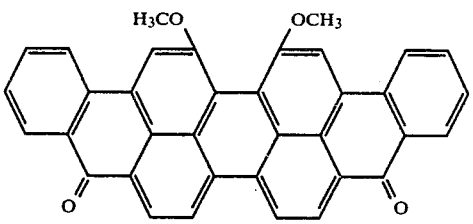

by reaction of the compound of the formula

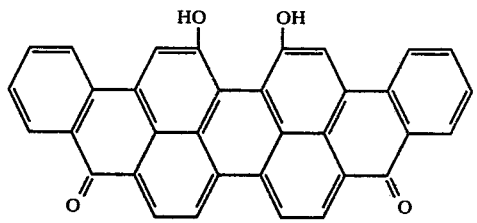

with dimethyl methanephosphonate of the formula

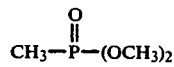

3. A process according to either of claims 1 or 2, wherein the reaction is carried out in the presence of a base or a mixture of bases.

4. A process according to claim 1, wherein the reaction is carried out in the presence or absence of a solvent or diluent.

5. A process according to claim 1, wherein the reaction is carried out at a temperature between 130° and 230° C.

* * * * *